United States Patent
Unetich et al.

(10) Patent No.: US 9,326,820 B2
(45) Date of Patent: May 3, 2016

(54) DIATHERMY APPLICATOR GARMENT

(71) Applicants: Robert M. Unetich, Pittsburgh, PA (US); Leslie R. J. Virany, Venetia, PA (US)

(72) Inventors: Robert M. Unetich, Pittsburgh, PA (US); Leslie R. J. Virany, Venetia, PA (US)

(73) Assignee: Regear Life Sciences Inc., Pittsburgh, PA (US)

( * ) Notice: Subject to any disclaimer, the term of this patent is extended or adjusted under 35 U.S.C. 154(b) by 449 days.

(21) Appl. No.: 13/933,347

(22) Filed: Jul. 2, 2013

(65) Prior Publication Data

US 2014/0018889 A1 Jan. 16, 2014

Related U.S. Application Data

(60) Provisional application No. 61/669,840, filed on Jul. 10, 2012.

(51) Int. Cl.
*A61B 18/18* (2006.01)
*A61N 1/40* (2006.01)
*A61N 2/02* (2006.01)

(52) U.S. Cl.
CPC ............. *A61B 18/18* (2013.01); *A61N 1/403* (2013.01); *A61N 2/02* (2013.01)

(58) Field of Classification Search
CPC ..................... A61F 7/007; A61F 2007/009
See application file for complete search history.

(56) References Cited

U.S. PATENT DOCUMENTS

| | | | |
|---|---|---|---|
| 6,922,579 B2 | 7/2005 | Taimisto | |
| 7,738,942 B2 | 6/2010 | Weiner | |
| 7,759,787 B2 | 7/2010 | Sri-Jayantha | |
| 2008/0312651 A1 | 12/2008 | Pope | |
| 2012/0253340 A1* | 10/2012 | Stevenson | H03H 7/0123 606/33 |

FOREIGN PATENT DOCUMENTS

WO WO 9948555 A1 * 9/1999 ......... A61N 1/36014

* cited by examiner

*Primary Examiner* — Joseph Stoklosa
*Assistant Examiner* — Nicole L Pobre
(74) *Attorney, Agent, or Firm* — Leslie R. J. Virany (57) ABSTRACT

A therapeutic diathermy applicator is proposed which minimizes the common problem of burning of patients' skin. The heat distribution arising as a result of unwanted capacitive effects is modeled as a manifestation of 'conservative' energy. A specific spatial characteristic of RF stimulation is determined and incorporated into the design of the applicator in order to achieve these goals.

9 Claims, 8 Drawing Sheets

DIATHERMY APPLICATOR GARMENT

FIELD OF THE INVENTION

The present invention pertains to improvements to manufacturing and operational methods for therapeutic diathermy treatment applicators as presented in prior commonly assigned U.S. Pat. Nos. 6,853,865, 7,953,500 and 8,489,201, all of which are herein expressly incorporated by reference in their entirety for essential subject matter.

The present invention relates to the field of diathermic treatment applicators.

GLOSSARY

Arg(z) angle of principle value of a complex number. (0</= Arg(z)</=2π)
Angles are given in radians unless otherwise noted.
Cauchy-Reimann Theorems pertaining to harmonic functions.
Conformal mapping: Complex mappings in which angles are preserved from the preimage region to the image region.
Derivative: slope
elbow: a point at which a curve changes direction abruptly
Euler's formula $e^{i\theta}$=cos θ+i sin θ thus $e^{\pi i}$=−1
EQS=electroquasistatic refers to oscillating electric fields which nevertheless retain many useful characteristics of static electric fields.
Extended complex plane: remains harmonic even at points at infinities and according to the theories of Cauchy and Reimann.
Fringe field: field distribution created at an end location of a finite-length boundary.
Harmonic: Complex generalization of the more common term "analytic," a term applied to continuous and differentiable functions.
"i": the square root of minus one
Isotherm: Lines of constant temperature
Laplace's equation: Pierre-Simon Laplace second-order partial differential equation, written as $\nabla^2_\phi 0=0$ where φ is a potential function.
Laplacian, Conservative, potential: fields, forces or flows conforming to Laplace's equation
Local extremum: a point where a function achieves a maximum or minimum value for some finite region of its domain
Mean Value Theorem of calculus: between any two points along a curve, there must be at least one point at which a tangent to the curve is parallel to a line connecting the two points.
Iterative Solution: 'solving' the unseparated equation in a form having the desired variable on both the left-hand side and the right-hand side, inserting an attempted value on the right-hand side, and repeating an attempted using result until it becomes apparent what value, if any, the solution converges to. steady-state spacing: periodic spacing of wire winding far from a fringe within a diathermy apparatus
MQS=magnetoquasistatic: as in EQS but for magnetic fields
Preimage: A region which is to be conformally mapped, typically designated by a complex number z
Schwartz-Christoffel mapping: a conformal mapping technique in complex analysis named after the mathematicians Elwin Bruno Christoffel and Hermann Amandus Schwarz.
w-plane, z-plane: complex planes where w=u+vi and z=x+yi for x, y, u, v real
Guidelines to these and other related concepts can be found for example in:
Fundamentals of Complex Analysis for Mathematics, Science, and Engineering Prentice-Hall 1976
Saff, E. B. & A. D. Snider

BACKGROUND OF THE INVENTION

Patients undergoing diathermic deep-heating treatment occasionally experience superficial burning to the skin surrounding the area of intended treatment, similar to sunburn. As treatment areas are internal, the skin area in question intervenes between the treatment area and source of RF energy. In particular RF burning does not appear to be the cause, as the measured increase in temperature at the actual intended treatment site is not more than a few degrees Fahrenheit. These and other observations lead applicants to conclude that burning is caused by electrical energy capacitively coupled through the wire insulation, wherein the capacitance value in question is determined substantially by the dielectric constant of the insulation at the RF frequency used in diathermy. (possibly as well as extraneous factors like air gaps which should be controlled by the fit of the garment and so on)

It is evident from experience, that in the case of diathermy, magnetic heating inside the therapeutic device, or deep heating, causes an increase in temperature of a few degrees at most. However, for an entirely different reason, patients occasionally experience superficial burning, somewhat resembling a sunburn. This burning affects only a top layer of skin.

Solutions entailing better insulation for applicator wiring are to some extent feasible but are expensive, do not completely solve the problem because they still have some capacitive coupling, and do not provide the same benefit to manufacturing with respect to other desirable characteristics of the insulation, such as bend radius. To some extent burning can also be reduced by proper choice of fabric material and thickness, especially local burning caused by a single turn of the wire as contrasted by relatively low heat applied in the space between two turns.

Statement of Problems with the Prior Art

The prior art has paid some attention to spacing, for example in U.S. Pat. No. 5,186,171 but without considering fringing effects. U.S. Pat. No. 4,964,415 attempts to absorb fringing fields but it requires an additional part, namely a 'radome' which must be selected with dielectric constant according to the specific patient and which furthermore considers only waveguide walls and not variation along the length of a diathermy applicator.

Electric fringing fields have also been calculated by conformal mapping. At the edge of a capacitor for example the upper plate must have constant voltage on its internal and external surface and also on the very endpoint of the plate. U.S. Pat. No. 6,490,920 teaches such a device, but the context lacks any discussion of thermal distributions produced by time-varying electromagnetic or RF stimulation and thus does not apply directly to the present invention.

Objects of the Invention

An object of the invention is the reduction of local surface burning during treatment by improving uniformity of capacitive coupling, without diminishing beneficial magnetic "deep" heating effects.

It is therefore apparent that therapeutic deep heating and unwanted surface heating arise from different sources and it is applicant goal to promote the former and eliminate the latter. For this reason it is necessary to consider in detail how the RF energy manifests itself in and around the area of treatment.

The source of the burning problem is that the temperature at the skin-fabric interface is not spatially constant. However, provided the temperature function is known here, Laplacian modeling will give the temperature distribution at other locations in the space of interest. The prior art does not take advantage of the mathematical Laplacian/Conservative mapping tools available for optimal spacing and for providing durable indicators.

SUMMARY OF THE INVENTION

Certain fields, forces and flows which may be well-modeled in mathematical physics are designated as 'conservative', 'potential', 'path-independent' or Laplacian. All these terms mean essentially the same thing for purposes of the present invention, namely that a given point has some energetic significance without memory of how it came to be of interest. A good example is the gravitational potential: the height of an object corresponds to a certain potential energy without any regard to whether it was, for example, lowered to that point or raised to that point. The same is true of a charge placed inside an electric field, such as the field inside a parallel-plate capacitor. The fact of interest is the distance between the charge and a plate, not how it got there.

Similar characteristics apply to a wide variety of magnetic behavior. An example of a case to the contrary is magnetic hysteresis, which exhibits a kind of memory. A specific example of a reason why this technique might not apply to an EM wave power distribution is the known negative thermal coefficient of wave impedance (substantially for all materials but metals) which leads for example to spotty heating in microwave ovens. Such phenomena are deemed not to play an important part with respect to the present invention.

In the case of situations which do properly admit of such a 'conservative force' solution, field lines exist which follow patterns like contours on maps, showing lines of constant "potential," in the case of electromagnetic phenomena, or constant temperature ('isotherms') in the case of heat flow.

Despite some departures from ideal conservative force behavior in diathermy, applicants have inventively analyzed the sources of good and bad energy and have devised appropriate means to substantially eliminate the latter without affecting the former.

DETAILED DESCRIPTION OF THE INVENTION

Applicants have inventively discovered that an appreciation of the precise dynamics of these fields and the attendant thermal flow leads to a clear determination of an optimal spacing for the wire winding. For one thing, diathermy employs RF stimulation, [see below: which is known not to be Conservative/Laplacian]. Thus the deformation of the spatial RF distribution under changing geometry must be treated differently and is more involved than the heat distribution.

Figure 1:
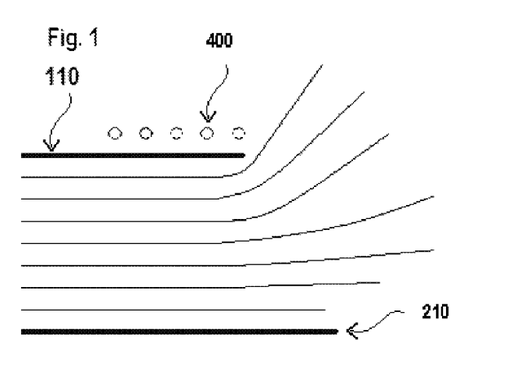
FIG. 1 Thermal distribution within an applicator garment given coil windings assumed to create a thermal boundary.

The surface with constant temperature may be regarded as a thermal boundary and deformations or other geometrical circumstances will be well-modeled by a conformal mapping of the heat distribution imposed by this boundary 110, regardless of the cause of the thermal boundary or its distribution along the length of the fabric, (or along a radial line, for the back garment) as shown in FIG. 1.

All (three) of the quantities in question in the present application of diathermic deep-heating all obey Laplacian rules. Included in this group are thermal, EQS fields and MQS fields. Of the three fields, primarily only the MQS is desirable. The beneficial heating is inductive. Undesirable fields include the EQS and the thermal surface distribution. (Thermal internal distribution by contrast, is the source of the intended therapeutic effect but, as will be explained, does not require careful consideration here) Therefore it is possible to accurately determine an optimal spacing pattern of the stimulating wires which accounts for fringing and other geometric irregularities of the applicator apparatus, as will be made plain below. In particular the bad surface heating and the good inductive heating can both be seen to be similarly Laplacian, so that the proposed steps to eliminate surface burning will not cause a functional reduction in deep heating, but will likely in fact cause a slight reduction in some areas though allowing an increase in amplitude, which does not lead to a significant change in deep-heating because of blood flow and so on as outlined elsewhere in this document.

The treatment applicator is based on the model of a solenoid, Unlike an ideal solenoid which is only perfectly-modeled as an infinitely-long winding of wires of infinitesimal thickness, applicant device comprises a few turns of relatively widely-spaced wire winding. Important differences exist but for purposes of the present document they may all be addressed by modifying the boundary 110 temperature distribution T as explained below in connection with FIG. 11.

The magnetic field inside the solenoid is given by an MQS-based center of a ring field which drops off as a power of distance from the wires. In the case of an infinitely-long solenoid with very narrow, closely-spaced wires, the field resembles that inside a perfectly-conducting cylinder.

Since it is generally known that the drop-off of magnetic energy measured away from a solenoid occurs faster than 1/r (the inverse of the distance to the observation point), the field may be modeled sufficiently well for present purposes as a magneto-quasistatic or MQS field. The direction of the magnetic field oscillates between the two opposite directions along the solenoid axis.

Justification for Modeling Techniques

Figure 7A:
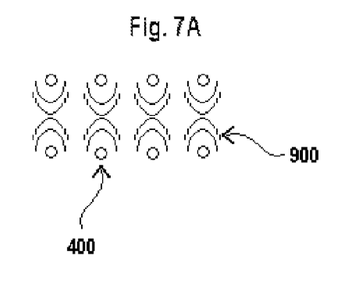
FIG. 7A Discrete cross section winding field distribution.
Figure 7B:
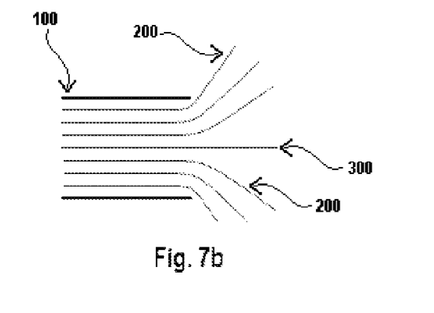
FIG. 7B Fringe field.

Referring to FIG. 7b, a condition of the validity of applicants' method is that the field lines (actually the 'potential function' from which the field lines are derived by performing a 'gradient' or other differential operation) in question must obey a Laplacian distribution. Examples of fields meeting this condition are heat, electrostatic potential and magnetostatic potential. The nature of these fields causes them to adopt clear configurations if the geometry is changed. In particular, if a parallel-plate capacitor is bent without any other changes being made, it is known that the bending does not change the voltages applied to the two plates 100.

For example if the upper plate of a capacitor with uniform dielectric (which is an example of a Laplacian field, in this case EQS) is held at 5 volts and a lower one is grounded, a charge in the middle 300 would be expected to be at 2.5 volts and remain so after bending. As the bending might cause local expanding or contraction of the plate separation however, a charge at an asymmetric point might end up slightly closer to one of the two plates.

This amounts to a deformation of the pattern of field lines 200. The deformation of the field lines may be described by a technique of 'conformal mapping' may be thought of as a mathematical analysis of how field or flow lines readjust because of a deformation. In the capacitor example, a voltage of 5 volts must remain on the upper plate whereas a voltage of 0 must remain on the lower.

Figure 11A:
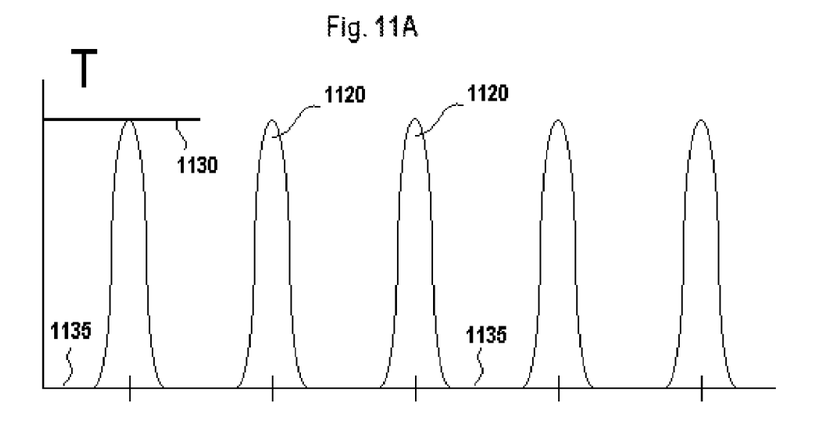
FIG. 11A Temperature distribution T(x) due to coil stimulation.

Thus, essentially the wire behaves like heating wire with a capacitance C depending on insulation, possibly another capacitance in series depending on skin $1/C_t=1/C_1+1/C_2$ and a further one representing fabric. The impedance Z, or resistance R is frequency-dependent, for fixed freq. in the neighborhood of one to three dozen megahertz. However the "uneven characteristic" is of importance in determining the form of the thermal boundary condition created by the EQS field, as depicted in FIG. 11*a*.

Owing to manufacturing difficulties in determining where each area of wire 1120 will wind up at the hot spot, applicants' use of a temperature distribution T is useful in that it may encompass these variations, as the solenoid departure described above, in a simple function modification. The problem is presented in simplified side view.

As a further inventive step applicants have observed that, insofar as some unwanted heating energy may be due to EQS rather than heat, the change in geometry produces the same change as both are mapped similarly. (since both are conservative)

Figure 2:
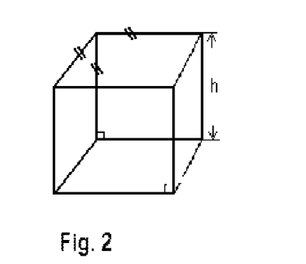
FIG. 2 Heat flow modeling of infinitesimal region.

FIG. 2 shows how an infinitesimal-tending square box works with the division of one large slab into a great number of very small pieces to illustrate Laplacian flow. As the limit of $(d\Phi\Delta\Phi)/(dx\Delta h)$ is taken to 0 where $\Phi$ is the heat potential and x is a dimension perpendicular to h, the limit approaches $d2\Phi/dx2$ or the second derivative, which when taken for all three dimensions gives Laplace's equation $\nabla^2\phi=0$.

Figure 3:
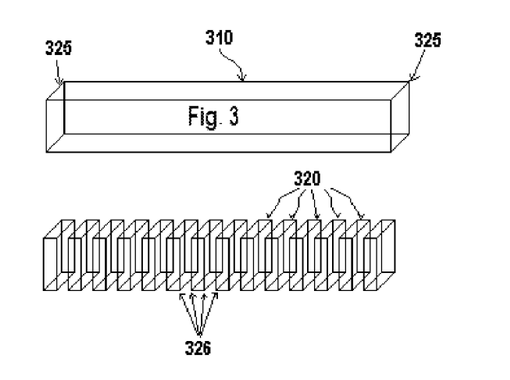
FIG. 3 Heat flow modeling showing finite region and subdivided finite region.

FIG. 3 shows why the conclusion that heat flow can be considered to respond to a spatially linear temperature gradient may be inferred from practical observation by considering an object of uniform material 310 characterized by a mass-dependent 'heat capacity'. In the absence of additional, internal heat sources or sinks, an increasingly finer division into a growing number of correspondingly smaller identical regions 320 connecting two thermal boundaries (i.e. T1 325, T2 325) must indistinguishably respond to their respective boundary conditions 326 imposed by adjacent such regions 320.

Figure 4:
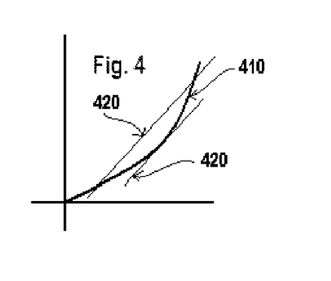
FIG. 4 Mean Value Theorem approximation technique.

FIG. 4 illustrates the Mean Value Theorem, which is useful in approximating curves 410 with simple lines 420 and implies that a first-order linear spatial heat flow relationship leads to 2nd-order spatial derivatives which, in 3D (and therefore of course also in fewer dimensions) is Laplacian.

It is known by the 2nd Law of Thermodynamics that, electrical power flowing into the closed region below the wire/fabric being a thermodynamic form of energy, in thermal equilibrium a 'constant' temperature must be established at each point along the wire. (though the temperature may not be the same for every point)

Consequently the focus of the invention is to regard the adverse heat in simplified form as being distributed away from an effective flat surface, (the fabric) wherein a Laplacian distribution describes the variation in heat along the (finite) extent of the heating surface and wherein this heat is produced by a steady state or temporally-constant temperature distribution as outlined above.

Figure 5:
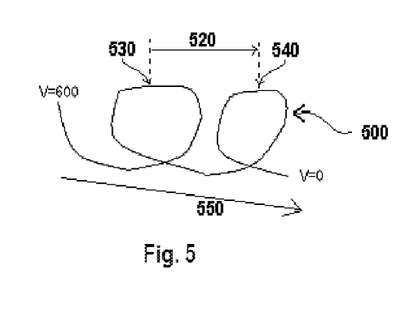
FIG. 5 Wire with constant voltage drop along its length.

FIG. 5 shows how the voltage, which is experimentally observed by the inventors to exhibit substantially constant voltage drop along its length, produces a varying point-to-point voltage drop 520 from one loop 530 to another 540 along a geodesic 550 drawn perpendicular to the wires along a surface in the diathermy device. Impedance along the coil 500 is calculated according to differential impedance dZ=dRπfdC for differential resistance dR, frequency f, distance d and intrinsic capacitance C. This capacitance exists between the wire and the patient skin 210.

Figure 6A:
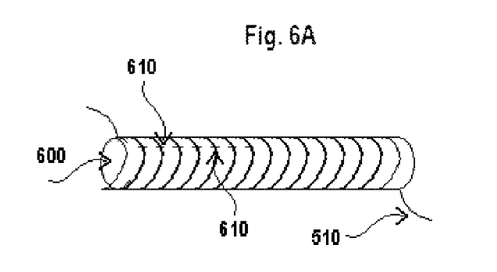
FIG. 6A Diathermy applicator cylindrical garment, wound with wire.
Figure 6B:
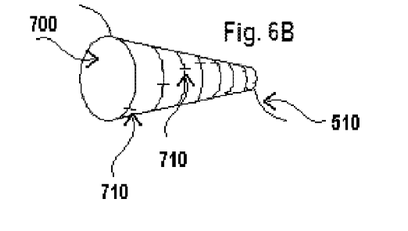
FIG. 6B Diathermy applicator conical garment, wound with wire.

As may readily be seen from FIGS. 6*a* & 6*b*, in contrast to the case of a cylindrical garment 600 with loops 610, the wire 510, when wound about a shape 700 of varying radius, will result in a varying loop-to-loop voltage drop for the conical shape since, starting at the narrow end, each successive wound loop 710 will encompass a smaller percentage of the cross-sectional circumference at the large end and a larger one at the small end. These voltage drops will lead to the general temperature distribution referred to as 'T' in the pre-image planes of FIG. 9*b* although the height variation corresponding to fabric flare is not shown.

The length of a given ring of the wire will thus vary according to 2π times the (varying) conical radius, and assuming a constant voltage drop per distance (since the drop is determined by the capacitances as outlined above) along the length of the wire, the heat produced at a given point is complicated and made further so by the presence of fringing, since the apparatus has distinctly finite length.

The effect of the conical shape, in the case of the limb-heating embodiment of the present invention, pertains only to the voltage drop along the heating wire. With respect to heat, at least the surface heat which applicant is trying to improve to the end outlined above for purposes of the present invention, unlike in the case of the EQS AND MQS fields, the shape does not affect the field distribution inside the solenoid. The reason for this difference is that the adverse heat in question falls off much more quickly than the diameter of the tube. (or distance away from the applicator, for the back garment)

The superimposed magnetic field 900 shown in FIG. 7*a* of a small to moderate number of consecutive rings 400, with finite spacing, follows the derivation of a solenoid even though it may retain an uneven characteristic.

The unevenness of the solenoidal field, though potentially attendant with some modeling challenges, (as described below in the form of the temperature function T(x)) is not considered to be of great consequence for the magnetic effects of applicants' heating device since blood flow and low heat gradients in tissue contribute to a smoothing of the beneficial MQS heating pattern.

Furthermore, as observed burning appears to occur most often near the center of the tube-shaped applicator. It appears that fringing may play an important part. By 'fringing' is meant the gradual drop-off of field intensities observed in a system in which the element providing an energetic or other boundary comes to an abrupt end. An example is the fringing field of two capacitor plates. See FIG. 7*b*.

Analysis of Model

Figure 8:
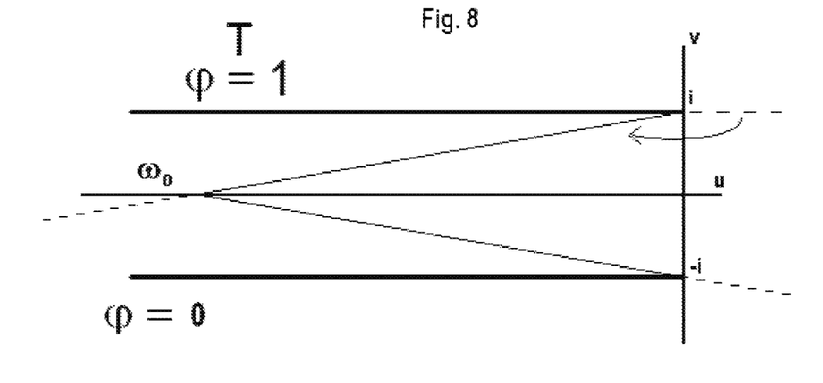
FIG. 8 "Extended complex plane" w(u,v) plane diagram showing points at infinities FIG. 9A Basic radial parametric preimaging.

FIG. 8 shows a geometry of the applicator fabric which receives the Schwartz-Christoffel mapping from the preimage plane below where A and B are selected to map the points 1,−1 to −i,i leading to the boundary conditions w(z=−1)=i and w(z=+1)=−i as explained above in the "Glossary" and below in the discussion referring to FIGS. 9a, 9b, 10 & 16:

$$w=f(z)=A(z+\log z)+B \quad (1)$$

$$w=f(z)=1/(i\pi-2)[2i(z+\log z)+\pi] \quad (2)$$

FIG. 8 shows an open polygon with vertex $w_0$ that tends to (negative) infinity in the extended complex plane, leading (except for the optional 3rd turn at bottom left) to the geometry associated with the physical problem of heat distribution in the diathermy apparatus. The top surface represents the (simplified, unwound) plane of the wires and the bottom surface represents the skin surface 210. Vertices map from points in a preimage plane (following the known method of Schwartz-Christoffel transformations)

$$w=1/(i\pi-2)[2i(re^{i\theta}-\log r-i\theta)+\pi] \quad (3)$$

$$w=u+iv$$

This allows selection of values for the constants A & B as shown in equations 1 & 2. Equation 3 substitutes a parametric polar representation for the general complex number 'z', thus allowing an easy reverse mapping of the preimage planes shown below.

$$u=-2/(4+\pi^2)[-2r\sin\theta-2\theta+\pi-\pi\cos\theta-\pi\log r] \quad (4)$$

$$v=-1/(4+\pi^2)[4r\cos\theta+4\log r-2\pi r\sin\theta-2\pi\theta+\pi^2] \quad (5)$$

The use of the above radial parametrization with the preimage planes yields a pattern of heat flow in the physical space of the diathermy apparatus.

Figure 9A:
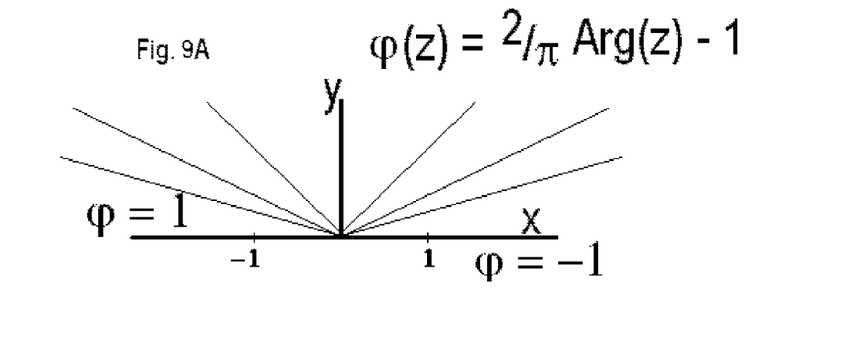
Figure 9B:
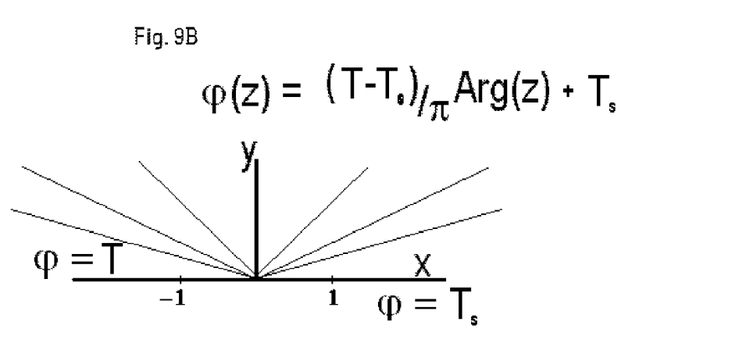
FIG. 9B Radial parametric preimaging of thermal boundary condition T(x)
Figure 10:
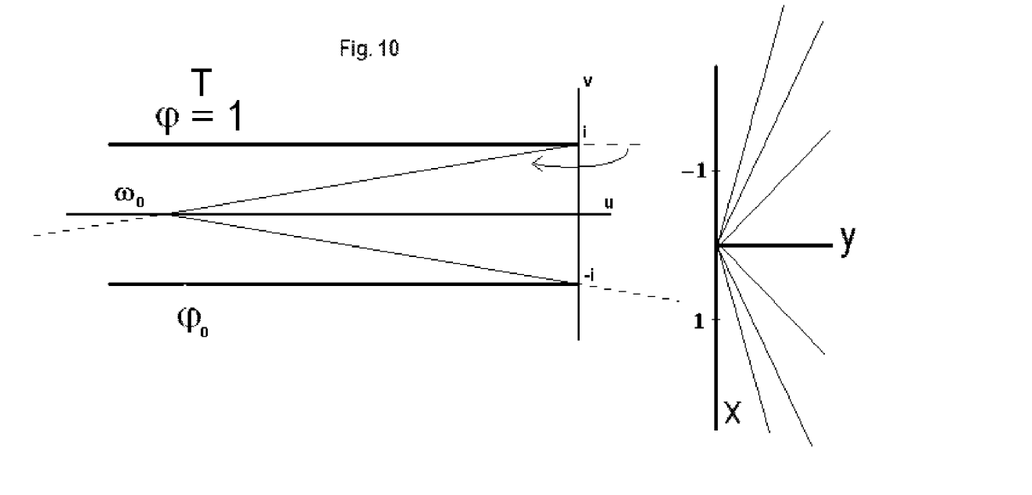
FIG. 10 Alignment of mapping and mapped planes.
Figure 16:
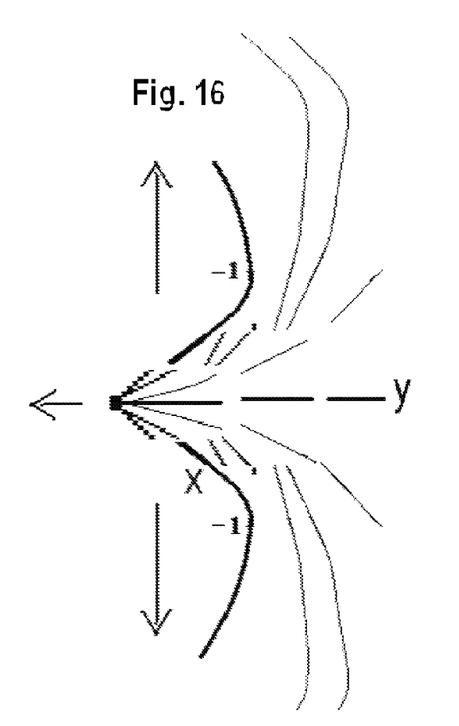
FIG. 16 Intermediate mapping showing continuous deformation.

FIGS. 9a & 10 show points 1 and −1 on the x-axis that map to points i and −1 on the v-axis and the temperature as a function of z FIG. 9b shows a preimage plane parametrizing radial lines that map (in the final geometry) to lines of constant temperature. FIG. 16 shows an intermediate mapping, with stretched y-axis and bent x-axis. Following convention 'arg' is taken to mean 'angle of principle value', or only values less than $2\pi$. This function (mapping) has radial symmetry in the plane z (=x+yi) and serves to carry an easily visualizable geometry via the inverse function into the w (=u+iv) plane of FIGS. 9 and 10. This may be seen by observing that any pure imaginary number of the form yi, with an angle of $\pi/2$ yields a value for $\psi$ of $(2/\pi)(\pi/2)-1$ which gives the value of 0 for the imaginary axis x=0. It is likewise for any other radial line.

Although the spikes and troughs of FIG. 11 indicate fundamentally only two voltage levels 1130, 1135 of interest, applicants propose that variations may arise from other effects (such as fabric 'flare' as indicated above, in which the garment fits imperfectly) however the actual form of this distribution may be encompassed in a general temperature function T(x) along the fabric which may be used with the mapping.

Figure 11B:
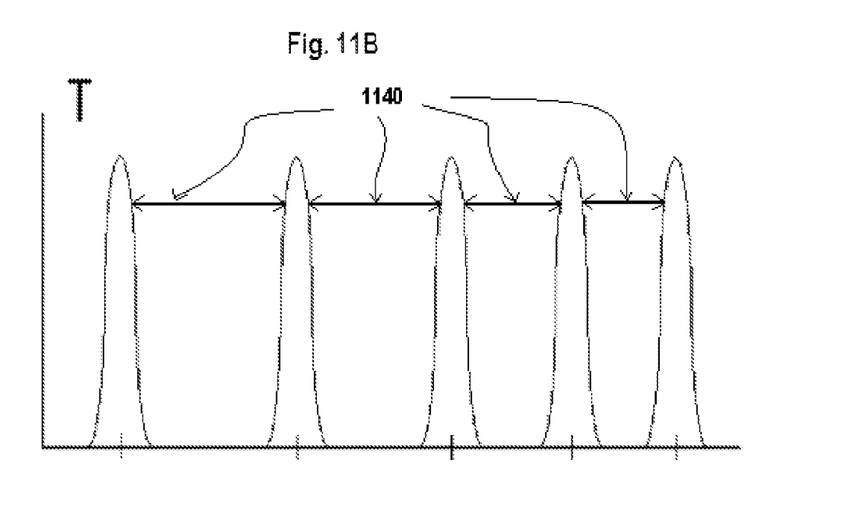
FIG. 11B Effect on temperature distribution T(x) due to unevenness of coil stimulation.

FIG. 11b shows how the preimage plane of FIG. 9b may be adapted for the present problem having a boundary temperature T imposed indirectly by wires as described above, i.e. NON-uniform wire spacing 1140 to contrast with FIG. 11a. T is given by some function depicted approximately in the graph, in which temperature spikes are created by the presence of wire 1130 and troughs by absence 1135, moving lengthwise along the surface of the diathermy garment.: Of course the heights may vary, in particular as discussed above in connection with varying voltage drops from one ring to another.

That the mappings correspond to the geometry indicated in FIG. 8 may be verified by inserting the value z=x+iy=0. Log 0 tending to minus infinity clearly maps to the indicated radius value shown as $r_0$.

A function giving the isotherms for the diathermic device in the geometry given above may therefore be constructed using the inverse mapping as $\phi(w)=\phi(u,v)=Arg(z)=Arg(x,y)=Arg[f^{-1}(w)]$ Thus the complicated isotherms in the diathermic apparatus plane derive from the simple radial lines shown in the foregoing diagram. Unfortunately, inverting the mapping algebraically is a very difficult task so it is necessary to gain some insight by graphical methods.

Figure 12:
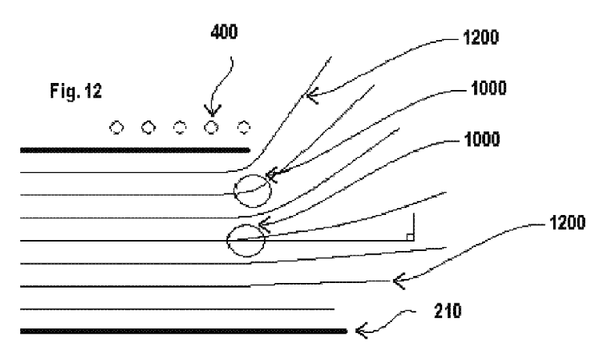
FIG. 12 Mapped thermal fields in fringe region.

FIG. 12 shows more clearly how the isotherms 1200 become more widely-spaced near the fringe. The isotherm distribution, far from the fringe, is completely linear and equispaced as long as the diathermy garment is of uniform material.

It is clear that points x=1,−1 map respectively to points w=−i, i as may be verified by again using Euler's formula to obtain $e^{\pi i}=-1$, giving a value of $i\pi$ for the (natural) log of −1.

FIG. 12 also shows how a clear idea of the practical extent of the fringe heat anomaly may be obtained: since each such line has a definite corner or 'elbow', the elbow 1000 corresponds to a point at which the angle of w(z) has a local maximum with respect to the parameter r from the preimage plane and thus this derivative goes to zero. The angle of this vector w drawn on the complex plane is given by $\tan^{-1}(v/u)$ where w=u+iv as before:

Thus a vector may be drawn in the w-plane with horizontal component given by u and vertical component given by v, for any angle $\theta$ and radius r. The complex number $w(z=re^{i\theta})$ may be rearranged through used of standard tools of complex algebra giving
i.e. a real part $$u=-2[-2r\sin\theta-2\theta+\pi-\pi r\cos\theta-\pi\log r]/(4+\pi^2) \quad (6)$$

and an imaginary part $$v=-[4r\cos\theta+4\log r-2\pi\sin\theta-2\pi\theta+\pi^2]/(4+\pi^2) \quad (7)$$

Some algebraic manipulation gives a location $r_0$ for an elbow 1000 (in the w-plane, as shown in FIG. 12) along any isotherm 1200 characterized by a radial line at angle $\theta$ in the z-plane (FIG. 9):

$$Angle[w]=\tan^{-1}[v/u]$$

$$2\sin\theta_0\log r_0+(\pi-2\theta_0)/r_0=(2\theta_0-\pi)\cos\theta_0+2\sin\theta_0 \quad (8)$$

which cannot be solved without numerical methods. However, traveling along the (middle) isotherm fixed by $\theta=\pi/2$, $z=r\,e^{i\pi/2}$, $w[\theta=\pi/2, r_0]$ $$0=d/dr\tan^{-1}\{v[\theta=\pi/2,r_0]/u[\theta=\pi/2,r_0]\}$$

allows a solution to be found for the case of this important isotherm;

$$\text{giving } r_0[\pi/2]=e \quad (9)$$

At the point $w[u_0(\theta=\pi/2), v_0(r_0=e)]$ $$u_0=[-2/(4+\pi^2)]*[-2e*1-\pi+\pi-\pi e*0-\pi] \text{ since }\log(e)=1$$

$$\text{or } u_0=[2/(4+\pi^2)]*[2e+\pi]=0.144*8.58=1.24$$

and $$v_0=[-1/(4+\pi^2)]*[4e*0+4-2\pi e-\pi^2+\pi^2]$$

$$\text{or } v_0=[-1/(4+\pi^2)]*[4-2\pi e]=-0.072*-13.1=0.942$$

Figure 15:
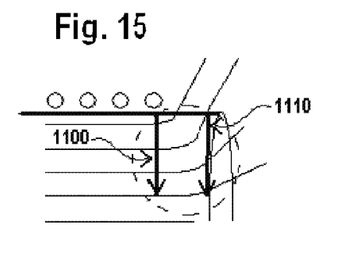
FIG. 15 Mapped thermal fields relating to wire spacing.

Thus a vector may be drawn in the w-plane with horizontal component given by $u_0$ and vertical component given by $v_0$, for this particular $\theta_0$ and $r_0$ and, referring to FIG. 15, it may be determined how many isotherms are crossed by a given vector 1100, 1110 at a given point along the diathermy applicator.

The complete expression for w is taken from the equation in the above diagram and, using Euler's formula allows an algebraic solution.

$$\tan^{-1}\{-\tfrac{1}{2}[4\log r - 2\pi r/(2r+\pi \log r)]\} \qquad (10)$$

$$\text{Angle}[w(r_0,\pi/2)] = \tan^{-1}[(\pi e-2)/(2e+\pi)] \qquad (11)$$

Application of Model in Solution of Problem

In particular, for $\theta=0, \pi, r=1$ as it must from the preimage plane as is reasoned as follows: these paths as shown in FIGS. 12 & 15 correspond to traveling along the two surfaces of the diathermy applicator and, since the isotherm must merge with the boundary in these cases. Thus a degenerate elbow is found at the point w=i where the preimage plane gives a radius of 1 along the real axis, pointing in the positive and negative directions respectively as is shown in FIG. 9.

That the points 1000 found for these elbows correspond to a maximum rather than a minimum, may be verified using further known methods of calculus. Along the single isotherm $\theta=\pi/2$ the expressions for u & v reduce to readily-solvable form as does the equation for the location of the elbow at given radius $r_0$. In particular $d/dr \tan^{-1}[v/u] = (udv/dr - vdu/dr)/(u^2+v^2)$ and the use of known techniques of differential algebra such as the 'chain rule' and 'quotient rule' and by taking note that the sign of the second derivative at the elbow is of use, rather than the exact equation, allows factors which are obviously positive (and therefore do not contribute to the sign) to be discarded. u & v are here given respectively by substituting $\theta=\pi/2$ in the above equations for u & v. As must be the case for a maximum (as opposed to a minimum) the second derivative at the point $r_0$, $\theta_0$ is negative.

Since z at this point is now determined, ($\theta$ being specified, r being constant for any $\theta$) w(z) may now be determined by the r,$\theta$ parametric mapping shown in FIG. 9b and given as Equation 3). Specifically the point, in the z-plane slightly to the right of the top right-hand corner of the diathermy applicator and down slightly less than half the way to the origin, the origin being halfway between the two thermal boundaries shown above. As is apparent from the above diagram, this value agrees strongly with the elbow shown in the isotherms drawn above, specifically the second one from the top surface of the applicator.

Two additional pieces of information which are of great interest in simplifying the final results may be gleaned from the Table 1 of elbow locations and graph data.

First, Table 1 shows that the isotherm expansion is very linear, as the elbow equation for values of $\theta$ in general cannot be solved in closed form. However, by taking the values at $\pi/2$ and another point, an intermediate approximation is found which, being attempted as an iterative solution of the general equation leads on the first attempt to a value within about 1%, where iteration in this case refers to 'solving' the unseparated equation in the form $r=e(f[r])$, inserting an attempted value for r in the exponential, and comparing the result with the attempt. Thus the isotherm $\theta=\pi/2$ may be regarded as representative of average heat loss from the outer surface of the garment to the inner surface, which distance is fixed by the choice of coordinates as the distance between v=i and v=−i, or a value of 2 times the unit distance, which itself is not fixed in physical units until the units of the heat gradient are established. (such as 'tens of degrees celsius per millimeter', as an example)

Second, since the angle of the isotherm is known by the above arctan equation at the elbow, a line may be approximated giving the average level of heat loss. (the difference between isotherm spacing for different locations along the axis of the diathermy applicator at two different locations in the neighborhood of the fringe)

The angle at the elbow is $\tan^{-1}[\pi e-2)/(2e+\pi)]$ or about 0.65 radians=37.4°.

so the average total heat loss for all isotherms is the same, owing to the above-described linear characteristic of and referring to FIG. 1.

Further, as each differential length on the wire provides approximately the same heating each point is similar, if not equivalent. Because of this (see below) heat variation in the dimension traversing the wire(s) may be dealt with by different means—fabric and insulation characteristics.

At the point w[$\theta=\pi/2, r_0=e$]

$$u_0 = 2[2e+\pi]/(4+\pi^2) = 0.144 \ast 8.58 = 1.24$$

and $$v_0 = 2[\pi e-2]/(4+\pi^2) = -0.072 \ast -13.1 = 0.942$$

$$V = \tan \gamma_0 \ast [e^{(u'-u_0')} - 1] + v'_0$$

where u' and v' essentially refer to the same space as is given by u and v previously, but are primed to indicate a real relationship as opposed to being complex parts. The values $\gamma_0=37.4°$, $\tan \gamma_0=0.765$, $u'_0=1.24$ and and $v'_0=0.942$ may be taken from the foregoing. This gives values of v on $\theta=\pi/2$ (the middle, which may be taken as the average) isotherm as follows in Table 1:

$$u' = \{-10, -5, -2, -1, -0.5, 0, 1, U'_0, 2\}$$

$$v' = \{0.177, 0.179, 0.206, 0.258, 0.311, 0.398, 0.779, V'_0, 1.81\}$$

TABLE 1

| $I^1$ | −10 | −5 | −2 | −1 | −.5 | 0 | 1 | $u'_0$ | 2 |
|---|---|---|---|---|---|---|---|---|---|
| $I^1$ | .177 | .179 | .206 | .258 | .311 | .398 | .779 | $v'_0$ | .1.81 |

Figure 14A:
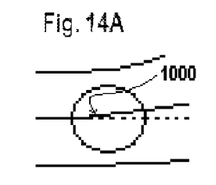
FIGS. 14A-14C Numerical methods.
Figure 14B:
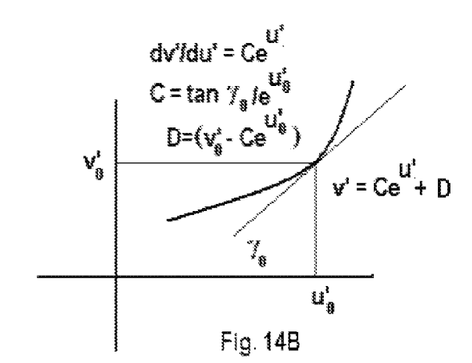
Figure 14C:
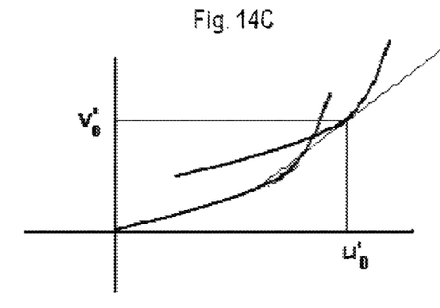

It should be noted that the value of v far from the fringe (corresponding to the middle of the diathermy applicator, halfway between the points −1 and i on the w-plane as shown in FIG. 8) should be 0. In fact with this exponential model it tends to a small value, (~0.177) which is an artifact of how the modeling curve is chosen. The artifact is illustrated in FIG. 14c: essentially the same shape curve shows a large vertical difference in leftmost final level, depending on whether it is made to fit the origin or the elbow point. However the relative decay, horizontally, is what determines how spacing should be adjusted.

Alternatively, rather than beginning with the slope 37.4° found at the point $u_0; v_0$, one may wish instead to pick, for the exponential model, an intermediate point between this main elbow and the garment fringe (at u=0) where the slope is, say, half at 18.7°.

Figure 17:
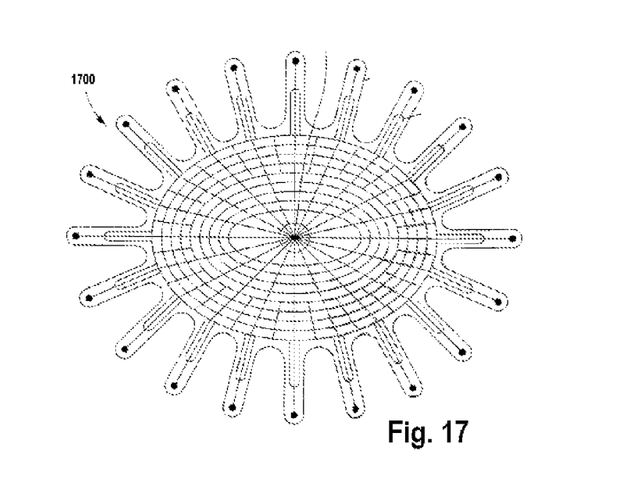
FIG. 17 Elliptical diathermy applicator garment.

The shape of the actual isotherm is governed by a more complicated equation thus it remains open to interpretation, how best to adjust the spacing to counteract nonuniform heating, and may depend on the type of applicator. (tube, conical, flat, elliptical 1700, composite such as the commonly-assigned shoulder applicator or even applicators integrated into a machine)

However, the present model nonetheless indicates approximately when the fringing effect becomes negligible; namely somewhere between u=−1 and u=−10. The variation at the fringe is about 3% although to the right it quickly goes to about 10%.

Implementation of Solution

The final goal of applicants' exercise, as outlined above, is of course to obtain a precise indication of how wire spacing ought to be advantageously adjusted in order to obtain minimal burning and maximal deep heating As a first step in practical implementation applicants observe that an indication of the scale of the isotherm density variation is given by the distance between two adjacent windings, (say "a characteristic distance $X_0$") which is defined in the spatial dependence of the temperature distribution T. It is a characteristic of conformal mapping that angles are preserved thus it may always be assumed that dimensionless vertical y and dimensionless horizontal x scale are identical unless steps are explicitly taken to provide a differently-scaled representation. Thus, if it is observed that, in a certain fringe region located, for example, "about one quarter of $X_0$ away from the last coil" isotherms appear to be "twice as far apart" as they are in the region far apart from any fringing effects, the prescribed remedy according to applicants' present invention is to compensate by approaching the two closest windings to this area by a factor of two.

The wire spacing should be adjusted to counteract the heat loss explained in the previous section.

Figure 13:
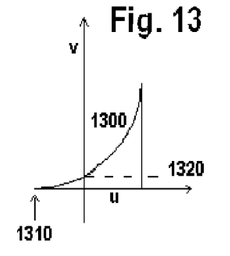
FIG. 13 Exponential approximation choices.

Thus the proper spacing variation may be inferred from the approximate exponential equation 1300 as shown in FIG. 13 and, as guided by the table, should be about the difference between the zero-value 1310 of v, namely 0.177 and its final value 1320 at u=0 (0.398) as a percentage of the unheated spacing. In other words the average space between two adjacent isotherms at the fringe is widened by an added factor of about 0.221 for 5/4 of what it was in spatial steady state. Thus remedial action is to make the spacing tighter at the fringe by the same factor, dropping to about 0.081, making for a tightening of about 13/12 at a distance u and substantially to one (its steady-state spacing) by a distance of 10 u. Observing likewise, the −2 u and −0.5 u separations, respectively, are about 0.029 and 0.134 for approximate respective tightenings of 3% and 13%. The spacing gradually reverts to its original value, as a function of distance away from the fringe, at a rate of .x or 10×% per unit distance. It should be noted that u=1 refers by w-plane coordinate definition to the half-height of the diathermy applicator fabric.

It should be noted that potential ambiguity due to 'fence-post errors' arising from how a wire should be displaced if the adjustment causes it to traverse the fringing boundary of the garment (i.e. become attached to the garment if it was not or vice versa) may simply be resolved by rotating the garment to find a location which lacks this ambiguity. Thus the present invention leads to a method of manufacture which may be implemented quickly and easily, with a minimum of specialized training necessary needed for manufacturing personnel.

The results of these modifications are in good agreement with applicants' observations that burning may be eliminated or substantially reduced by providing a higher density of Wire spacing near the end of the diathermy garment and lower density of spacing near the middle.

It should further be noted that this spacing applies anywhere wire is encountered perpendicularly, as shown in FIG. 15. Moving along a geodesic towards any fringe on any diathermy applicator in which the fringe consists of a termination of heating rather than, as is for example mentioned elsewhere in this document, an abutting plane of increased heating such as might be constructed for specific body areas such as feet or shoulders. As a further illustration of this point, a diathermy hand garment as disclosed in applicants' incorporated references suggests fringes of both types: wrist and open fingers represent fringes of the type herein discussed whereas a closed finger sock, for example, would abut against increased heating at the fingertip and would therefore have to be treated by other methods.

Those experienced in the field of this invention should, based on the detailed descriptions of the objectives and new methods, be able to understand the logical possible variations. They will be able to adopt appropriate strategies, dimensions and geometries depending on the various applications and needs of different diathermy applicators, not specifically shown in this application, but within the general goals and objectives of this invention.

The invention claimed is:

1. A diathermy applicator garment comprising RF stimulation produced by a sequence of coils of a continuous conductor wherein
said coils are wound with respect to an axis and wherein
said coils reach a termination and wherein
spacing of said coils is varied approaching said termination and wherein further at least one point along said conductor is characterized according to a distance u measured from said termination along the length of the applicator and wherein spacing of said point with respect to point of its nearest section of greater u is reduced according to a perturbation factor v' from an evenly distributed spacing and wherein further v' is determined according to the table $u=\{10,5,2,1,5,0\}$ $v'=\{0.177, 0.179, 0.206, 0.258, 0.311, 0.398\}$.

2. The diathermy applicator garment of claim 1 wherein a target for said RF stimulation is a target designated for medical treatment.

3. The diathermy applicator garment of claim 1 wherein the surface of said RF radiation target is skin.

4. The diathermy applicator garment of claim 3 wherein further v' is determined according to the equation $v'=\tan \gamma_0 * [e^{(u'-u_0')}-1]+v'_0$ and wherein u' is a perturbed distance measured from said termination along the length of the applicator at a surface of said skin and
where $u'_0$ is approximately 1.24 and
where $v'_0$ is approximately 0.942 and
where $\gamma_0$ is approximately 37.4°.

5. The diathermy applicator garment of claim 3 wherein at least a portion of the coils of said garment are wound substantially in the shape of a cylinder and said axis is parallel to the axis of said cylinder.

6. The diathermy applicator garment of claim 3 wherein at least a portion of the coils of said garment are wound substantially in the shape of a cone and said axis is parallel to the axis of said cone.

7. The diathermy applicator garment of claim 3 wherein at least a portion of the coils of said garment are wound substantially in the shape of an ellipse and said axis is perpendicular to a diameter of said ellipse.

8. The diathermy applicator garment of claim 3 wherein said RF radiation target is an area designated for warming of a body part in a cold environment.

9. The diathermy applicator garment of claim 3 wherein at least a portion of the coils of said garment are wound substantially in the shape of a circle and said axis is perpendicular to a diameter of said circle.

* * * * *